US009883977B1

(12) United States Patent
Cooper

(10) Patent No.: US 9,883,977 B1
(45) Date of Patent: Feb. 6, 2018

(54) DIAPER WITH BOWEL POCKET

(71) Applicant: Wendy K. Cooper, Hamilton (CA)

(72) Inventor: Wendy K. Cooper, Hamilton (CA)

( * ) Notice: Subject to any disclaimer, the term of this patent is extended or adjusted under 35 U.S.C. 154(b) by 639 days.

(21) Appl. No.: 14/295,909

(22) Filed: Jun. 4, 2014

Related U.S. Application Data

(60) Provisional application No. 61/897,539, filed on Oct. 30, 2013.

(51) Int. Cl.
*A61F 13/15* (2006.01)
*A61F 13/505* (2006.01)
*A61F 13/495* (2006.01)

(52) U.S. Cl.
CPC .......... *A61F 13/505* (2013.01); *A61F 13/495* (2013.01); *A61F 2013/4951* (2013.01); *A61F 2013/4953* (2013.01); *A61F 2013/4956* (2013.01); *A61F 2013/4958* (2013.01)

(58) Field of Classification Search
CPC ............ A61F 13/495; A61F 2013/4951; A61F 2013/4953; A61F 2013/4956; A61F 2013/4958
USPC .................. 604/348, 385.14, 385.01, 385.21
See application file for complete search history.

(56) References Cited

U.S. PATENT DOCUMENTS

| 4,784,656 A | 11/1988 | Christian |
| 4,834,737 A | 5/1989 | Khan |
| 4,834,741 A | 5/1989 | Sabee |
| 4,892,536 A | 1/1990 | DesMarais et al. |
| 5,527,302 A | 6/1996 | Endres et al. |
| 6,132,409 A | 10/2000 | Vogt et al. |
| 6,258,076 B1 * | 7/2001 | Glaug ............... A61F 13/49466 604/385.01 |
| 6,468,256 B1 | 10/2002 | Mishima |
| 6,951,552 B2 | 10/2005 | D'Acchioli et al. |
| 7,316,674 B2 * | 1/2008 | Infantino .......... A61F 13/49466 604/385.01 |

FOREIGN PATENT DOCUMENTS

EP          0498612 A1    8/1992

* cited by examiner

*Primary Examiner* — Jacqueline Stephens
(74) *Attorney, Agent, or Firm* — Robert C Montgomery; Montgomery Patent and Design

(57) ABSTRACT

A diaper insert has specifically configured contours on an inside surface to trap and contain bowel movements delivered within the diaper. An upper rear portion of the insert provides a protruding section of absorbent padding being contoured to match a lower lumbar region of the wearer. An upper front portion of the insert is provided with an additional absorbent pad to abut the abdominal area of the wearer. When a user, wearing a diaper equipped with the insert experiences a bowel movement, the padding sections contain the bowel movement within the diaper, and prevent the bowel movement from being secreted from a waist area of the diaper. In at least one (1) embodiment the insert is manufactured to be an integral portion of a diaper. In at least one (1) embodiment unitary rear and front barriers are removably added to a diaper.

11 Claims, 7 Drawing Sheets

DIAPER WITH BOWEL POCKET

RELATED APPLICATIONS

The present invention was first described in and claims the benefit of U.S. Provisional Application No. 61/897,539, filed Oct. 30, 2013, the entire disclosures of which are incorporated herein by reference.

FIELD OF THE INVENTION

The present invention relates generally to a diaper with an insert having specifically configured contours on an inside surface to trap and contain bowel movements delivered within the diaper.

BACKGROUND OF THE INVENTION

Diapers have been a lifesaver to parents and care providers of young children as well as adults suffering from incontinence. They provide a handy and sanitary means of controlling feces and urine for both the user and care provider alike. However, even the best diaper is no match for containing a bowel movement when the user is in a seated position. Such a position places pressure on the diaper forcing the bowel movement to exit through the waistband area. Such leakage can easily ruin clothes, but also other items that are more difficult to clean such as carpeting, furniture, car seats, and the like. Additionally, such leakage is extremely messy, and time-consuming to clean up. Accordingly, there exists a need for a means by which diaper leakage from a bowel movement can be easily contained, in order to address the problems as described above.

The invention is also very useful for infants up to adults while lying in bed if they have very loose bowel movements or diarrhea. It is also helpful in use in hospitals and daycare centers to aid in containing an outbreak. The use of the present invention reduces/eliminates the occurrences of diaper leakage in a manner which is quick, easy, and effective.

SUMMARY OF THE INVENTION

The disadvantages of the prior art are overcome by the present invention in providing a diaper insert that has specifically configured contours on an inside surface to trap and contain bowel movements delivered within the diaper. An upper rear portion of the insert provides a protruding section of absorbent padding being contoured to match a lower lumbar region of the wearer. An upper front portion of the insert is provided with an additional absorbent pad to abut the abdominal area of the wearer. When a user, wearing a diaper equipped with the insert experiences a bowel movement, the padding sections contain the bowel movement within the diaper, and prevent the bowel movement from being secreted from a waist area of the diaper. An alternate embodiment incorporates the containing features of the insert into the diaper assembly during manufacturing. In this manner, the use of the present invention provides a means preventing the problems relating to the prior art.

In at least one (1) embodiment the insert is manufactured to be an integral portion of a diaper.

In at least one (1) embodiment unitary rear and front barriers are removably added to a diaper.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

Figure 1:
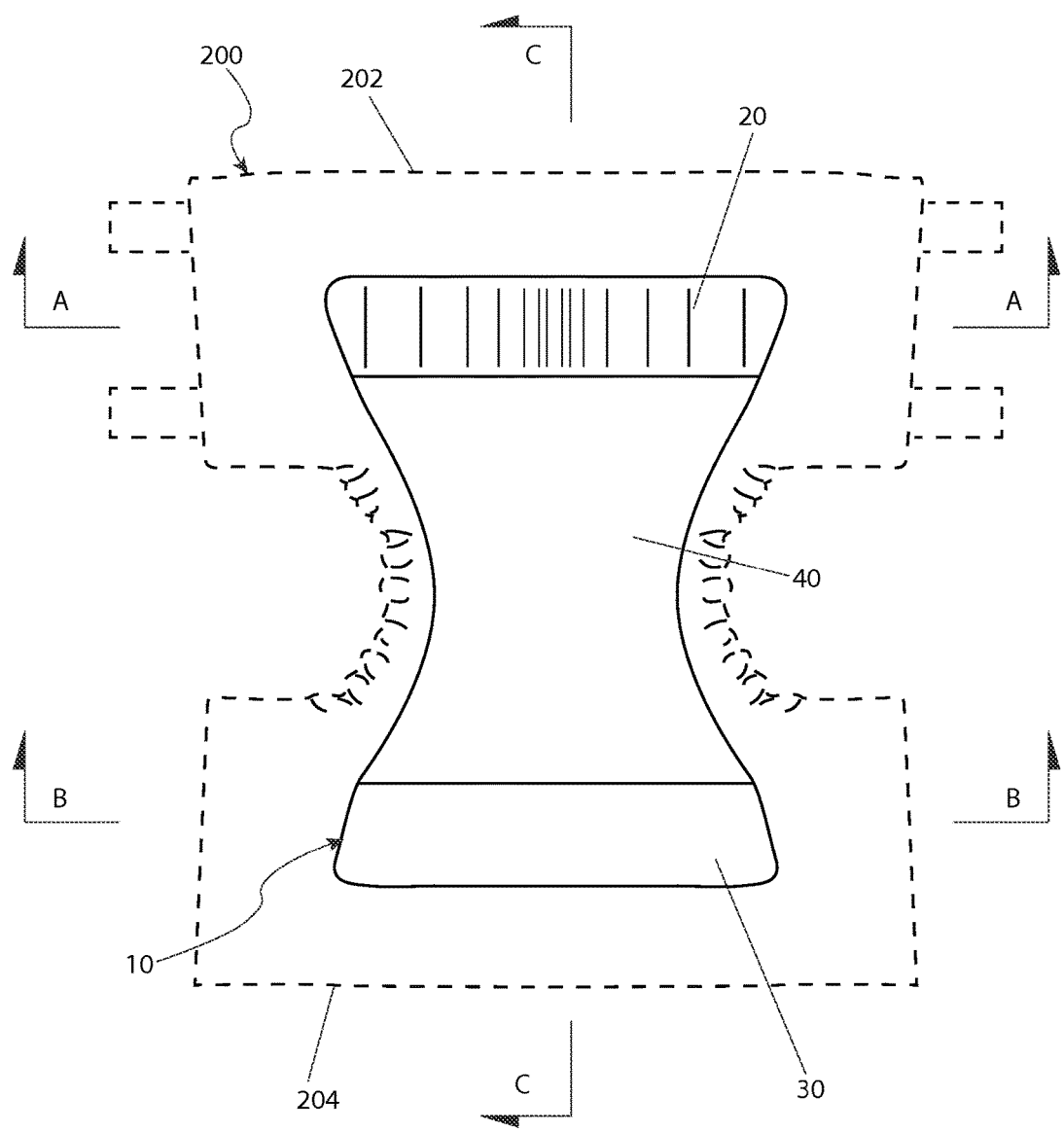
FIG. 1 is a top view of a containment insert for a diaper 10, according to a preferred embodiment of the present invention.

DESCRIPTIVE KEY 10 containment insert
20 rear barrier
22 center protrusion
24a first adhesive strip
24b second adhesive strip
24c third adhesive strip
26 wax paper
30 front barrier
40 insert panel
50 torso
52 lumbar region
53 abdominal region
100 first alternate embodiment
200 diaper assembly
202 rear waistband
204 front waistband
205 rear wing
206 front wing
208 elastic leg opening
210 tape fastener
220 alternate rear barrier
230 alternate front barrier
240 alternate insert panel
300 second alternate embodiment
310 unitary rear barrier
320 unitary front barrier
330 unitary adhesive strip

DETAILED DESCRIPTION OF THE PREFERRED EMBODIMENT

Figure 2:
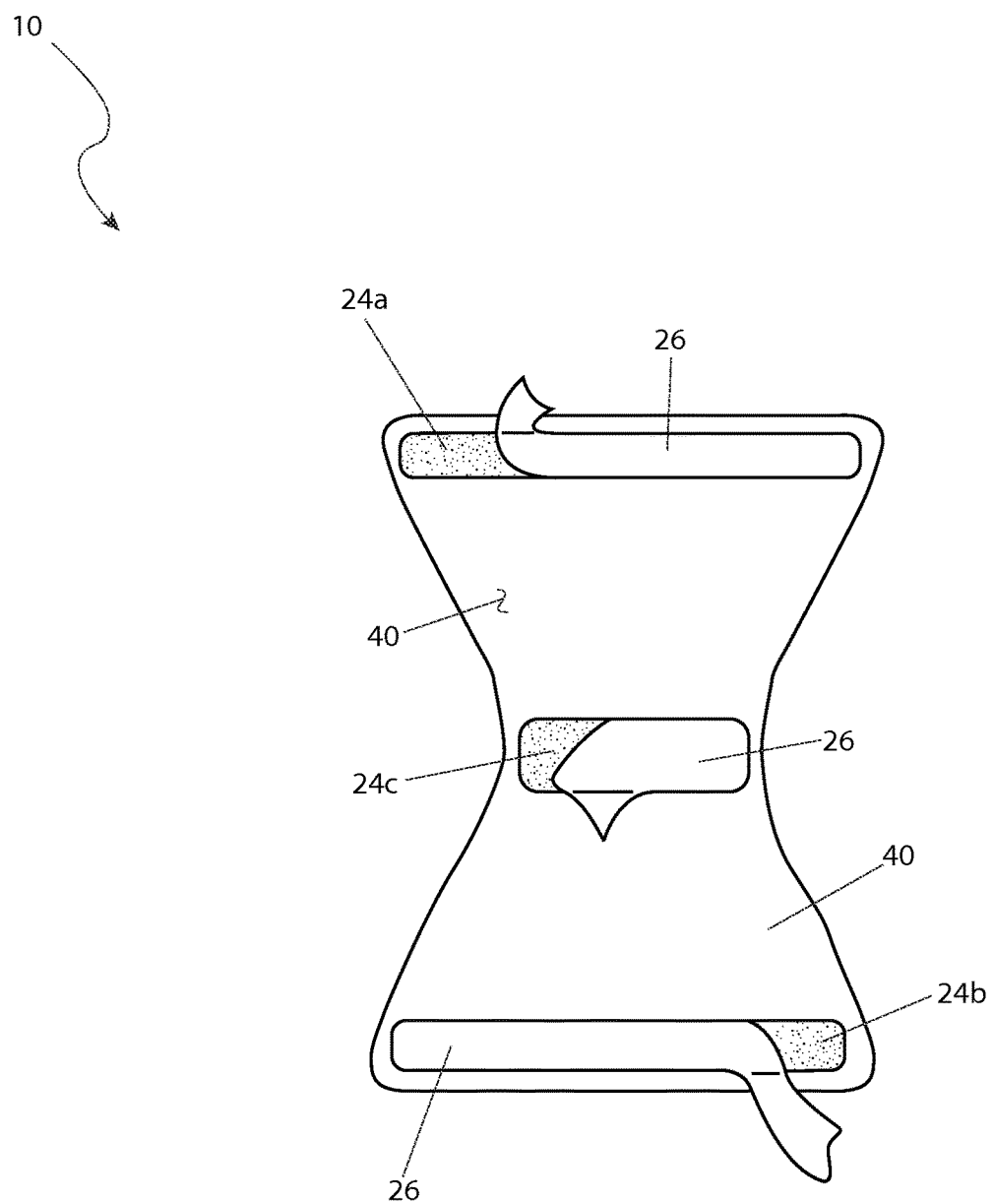
FIG. 2 is a bottom view of the containment insert for a diaper 10, according to a preferred embodiment of the present invention.
Figure 3A:
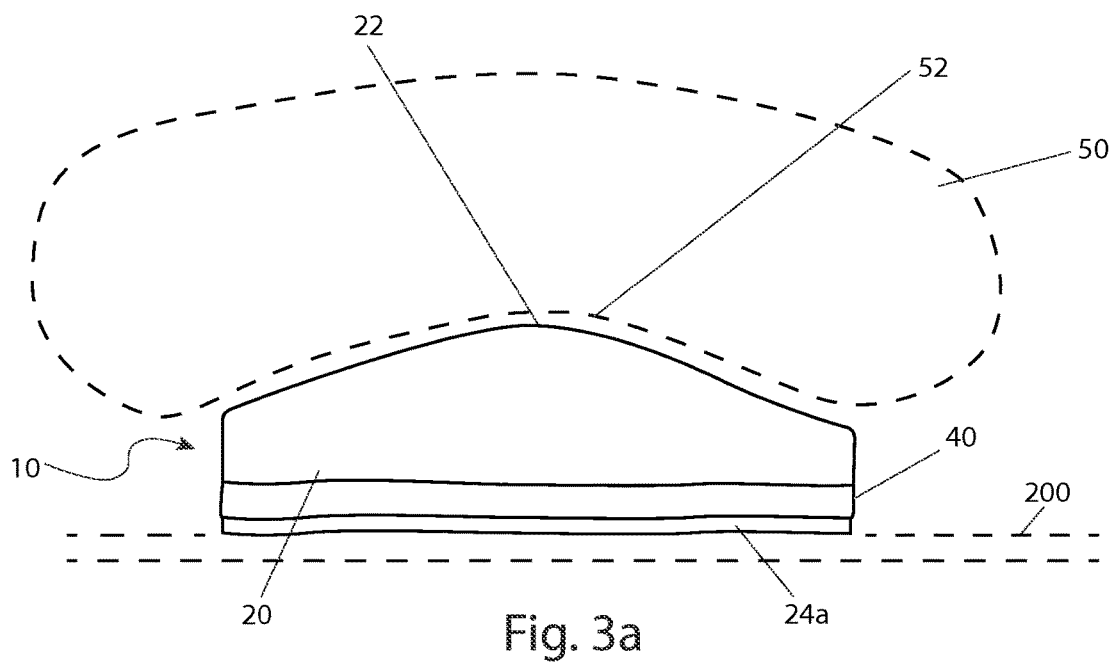
FIG. 3a is a sectional view of the containment insert for a diaper 10 taken along section line A-A (see FIG. 1), according to a preferred embodiment of the present invention.
Figure 3B:
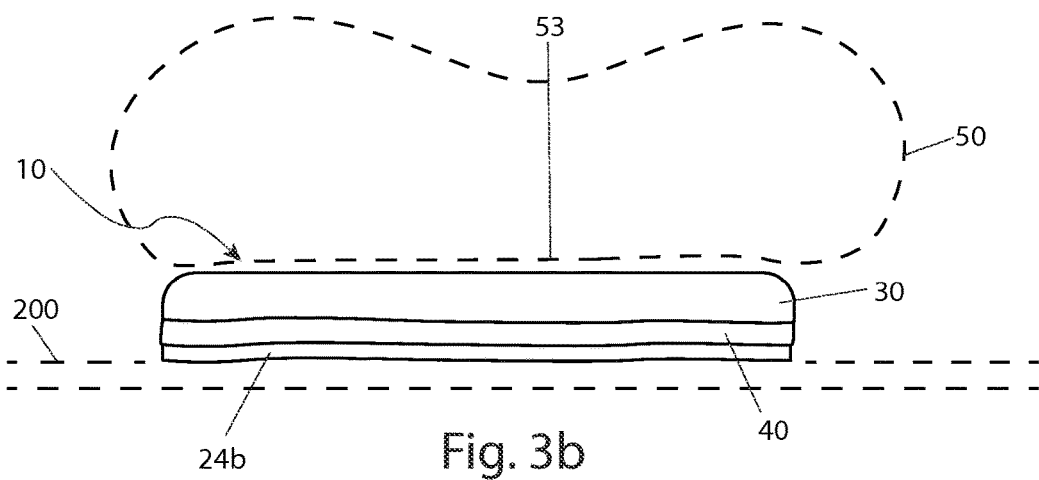
FIG. 3b is another sectional view of the containment insert for a diaper 10 taken along section line B-B (see FIG. 1), according to a preferred embodiment of the present invention.
Figure 3C:
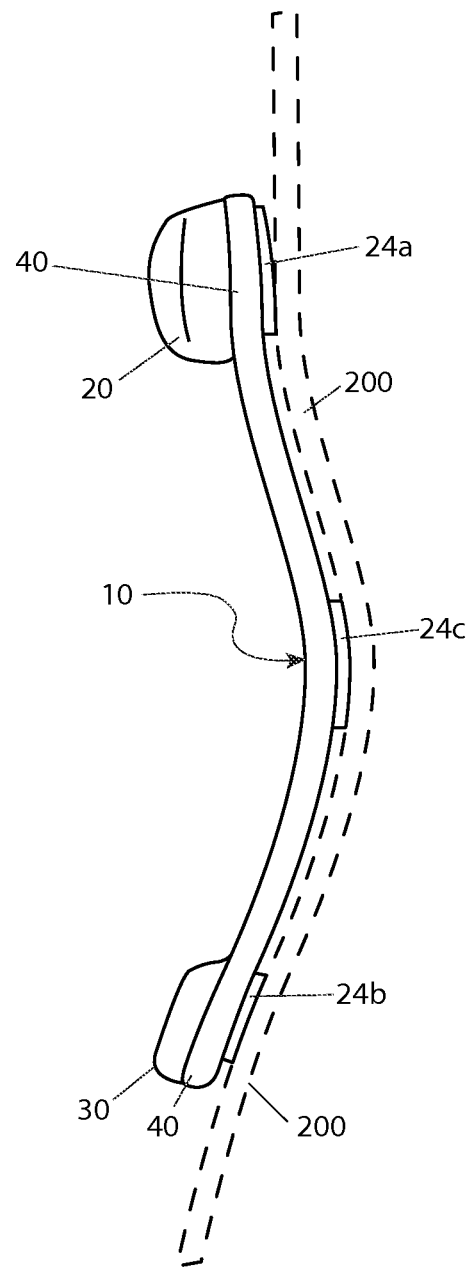
FIG. 3c is yet another sectional view of the containment insert for a diaper 10 taken along section line C-C (see FIG. 1), according to a preferred embodiment of the present invention.
Figure 4:
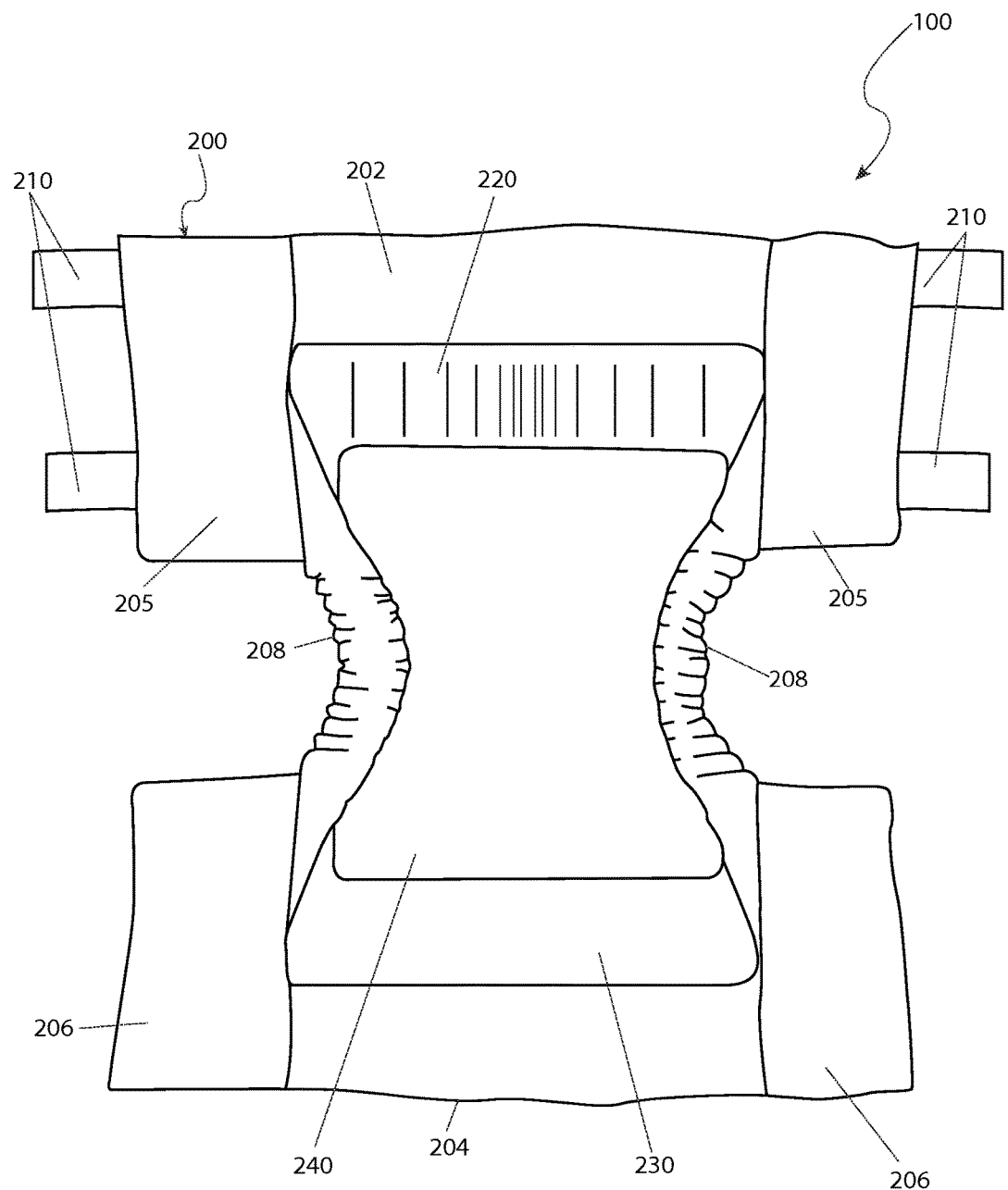
FIG. 4 is a top view of a first alternate embodiment 100 of the present invention depicting integration of the present invention into a conventional diaper assembly 200.
Figure 5A:
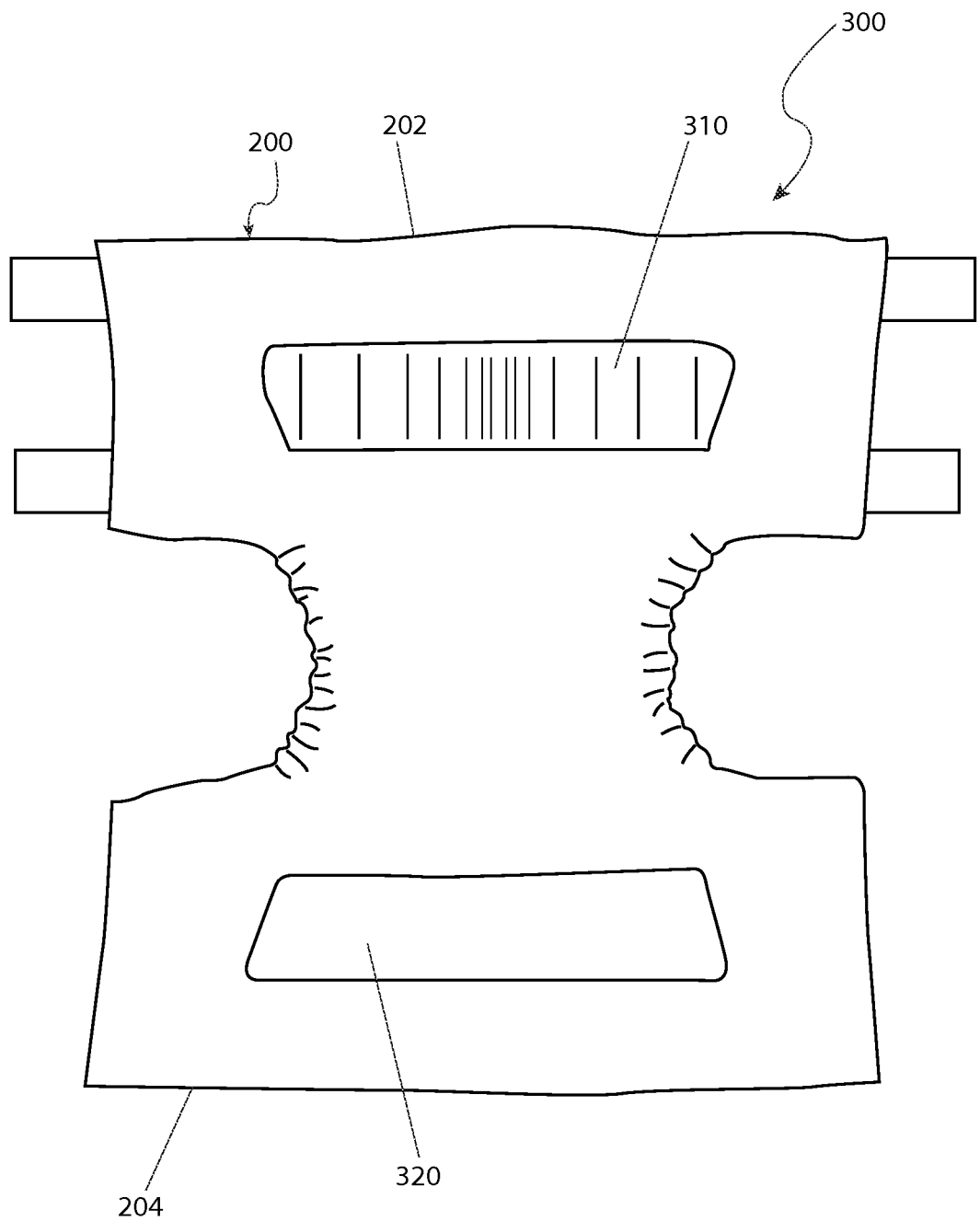
FIG. 5a is a top view of a second alternate embodiment 300 of the invention.
Figure 5B:
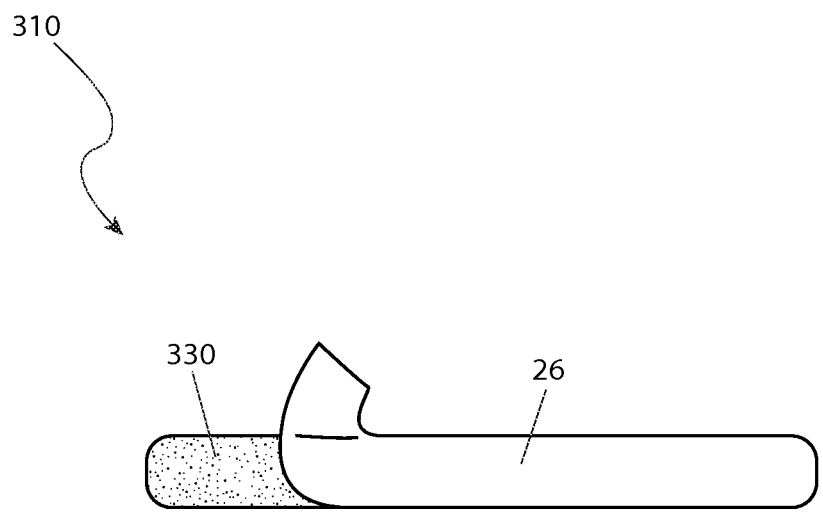
FIG. 5b is a bottom view of a unitary rear barrier portion 310 of the second alternate embodiment 300 of the invention; and, FIG. 5c is a bottom view of a unitary front barrier portion 320 of the second alternate embodiment 300 of the invention.
Figure 5C:
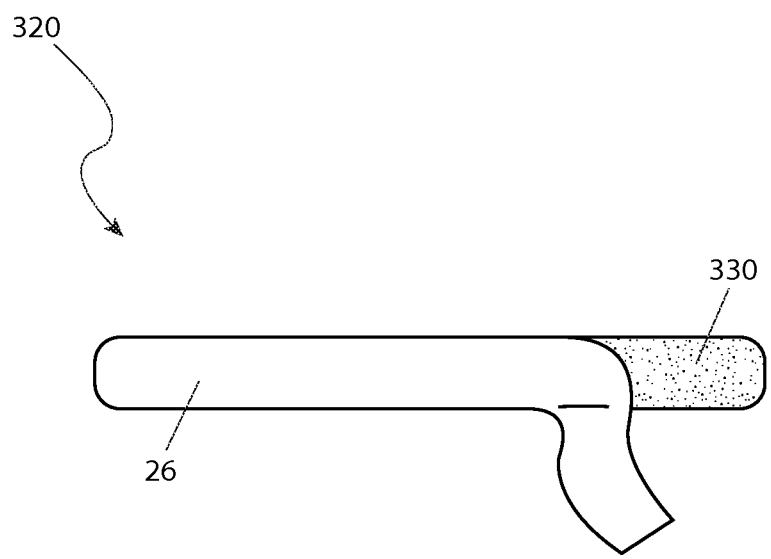

The best mode for carrying out the invention is presented in terms of its preferred embodiment, herein depicted within FIGS. 1 through 3c and in terms of alternate embodiments, herein depicted in FIGS. 4 through 5c. A person skilled in the art will appreciate that many other embodiments of the invention are possible without deviating from the basic concept of the invention. Any such work around will also fall under scope of this invention. While only one particular configuration is shown and described that is for purposes of clarity and disclosure and not by way of limitation of scope.

The present invention describes a containment insert for a diaper (herein described as the "device") 10, to be installed within an existing diaper assembly 200 prior to use upon a wearer. The device 10 provides features to aid in the retention of a bowel movement, by preventing migration of said bowel movement beyond waistband areas 202, 204 and out of the diaper assembly 200.

Referring now to FIGS. 1 and 2, top and bottom views of the device 10, according to a preferred embodiment of the present invention, are disclosed. The device 10 comprises an hour-glass-shaped insert panel 40 having integral rear bather 20 and front barrier 30 portions positioned at respective end portions of an inwardly-facing surface of said insert panel 40. The barriers 20, 30 provide outwardly protruding forms capable of absorbing body fluids as well as acting as mechanical appendages to prevent migration of a bowel movement out of an existing diaper assembly 200.

The rear barrier 20 comprises an elevated and generally inverted "V"-shaped form which extends laterally across a wearer's lower back lumbar region 52. The rear barrier 20 is designed to provide an elevated center protrusion 22 configured to correspond to a recessed contour of a lumbar region 52 of a wearer's torso 50. The containment insert 10 further comprises a front barrier 30 which extends laterally across a wearers abdominal region 53 to provide additional containment of the bowel movement. The barriers 20, 30 are to be made of soft absorbent natural and synthetic materials such as polypropylene, cotton batt, sodium polyacrylate, and the like, being affixed to a joining insert panel 40 which in turn extends down and around a buttock portion of the wearer being adhesively affixed to, and parallel to, the existing diaper assembly 200. Alternately, the barriers 20, 30 can be affixed to the insert panel 40 via other fastening means, such as Velcro®.

The insert panel 40 includes a fabric panel having an hour-glass perimeter shape when lying flat, made of similar materials as the barriers 20, 30 to provide additional absorbency to supplement that of the subjacent diaper assembly 200. The insert panel 40 retains and positions the barriers 20, 30 as well as providing a means to attach the device 10 to the diaper assembly 200 via three (3) equally-spaced lateral adhesive strips 24a, 24b, 24c located upon an outward-facing surface of the insert panel 40. A first adhesive strip 24a is located behind the rear bather 20, a second adhesive strip 24b is positioned behind the front barrier 30, and a third adhesive strip 24c is located approximately half way between the first 24a and second 24b adhesive strips. The adhesive strips 24a, 24b, 24c are envisioned to be covered by wax paper 26 which is pulled off at time of use. Alternately, the insert panel 40 can be affixed to the diaper assembly 200 via other fastening means, such as Velcro®.

It is envisioned that the device 10 would be introduced in various sizes for use with small children up to large adults, thereby providing proportionally sized barrier portions 20, 30 and insert panel 40 features. It is envisioned that as the diaper assembly 200 and device 10 sizes increase, the outer end and center portions of the rear barrier 20 would increase at approximately a one to two (1:2) ratio, respectively. It is further envisioned that the curved shape of the diaper assembly 200 along with the positioning of the barriers 20, 30, would form a pocket-shaped recessed area which would hold a bowel movement in lieu of having it move upwards, and out of a waistband 202, 204. The device 10 is envisioned to be ideal for use with infants that spend a great deal of time in a stroller, car seat, infant swing, or similar apparatus. The device 10 is also ideal for incontinent adults who spend a long time in a seated position, or in a wheelchair. The device 10 is envisioned to greatly reduce cleanup duties for the wearer and/or a care provider. It is envisioned that the device 10 be introduced for sale being packaged as single units as well as in various convenient quantities in a similar manner as common diapers 200.

Referring now to FIGS. 3a, 3b, and 3c, sectional views of the device 10, according to the preferred embodiment of the present invention, are disclosed. The rear barrier 20 is illustrated in FIG. 3a having a profile which conforms to a recessed contour of a lumbar region 52 of a wearer's torso 50. The rear barrier 20 is permanently affixed to the insert panel 40 using common methods such as sewing, adhesive bonding, radio frequency (RF) welding, or the like. The insert panel 40 is in turn affixed to the existing diaper assembly 200 via the first adhesive strips 24a, 24b, 24c.

The front barrier 30 is illustrated in FIG. 3b having a flat profile, conforming to a forward abdominal region 53 of a wearer's torso 50. The front barrier 30 comprises similar construction as the rear barrier 20 and is affixed to the diaper assembly 200 in a like manner. The insert panel 40 is adhesively affixed to the existing diaper assembly 200 via the adhesive strips 24a, 24b, 24c (as seen in FIG. 3c). The insert panel portion 40 of the device 10 conforms to the curvature of the diaper assembly 200 when installed and affixed to the wearer.

Referring now to FIG. 4, a top view of a first alternate embodiment 100 of the present invention depicting integration of the present invention into a conventional diaper assembly 200, is disclosed. The first alternate embodiment 100 depicts the present invention 10 being integrated into the construction of the diaper assembly 200 using common methods such as sewing, adhesive bonding, RF welding, or the like during initial manufacturing of the diaper assembly 200. The diaper assembly 200 is illustrated here including a rear waistband 202, a front waistband 204, a pair of rear wings 205, a pair of front wings 206, a pair of elastic leg openings 208, and a plurality of tape fasteners 210. The first alternate embodiment 100 is further envisioned to include similar portions as the preferred embodiment 10 including an alternate rear barrier 220, an alternate front barrier 230, and an alternate insert panel 240. Said alternate portions 220, 230, 240 are to provide similar absorbency and mechanical containment functions as the respective counterparts of the previously described preferred embodiment 10.

Referring now to FIGS. 5a, 5b, and 5c, top and bottom views of unitary rear barrier 310 and unitary front barrier 320 portions of a second alternate embodiment 300 of the invention, are disclosed. The second alternate embodiment 300 provides unitary rear barrier 310 and unitary front barrier 320 portions being similar in shape and profile as the previously described preferred rear barrier 20 and front barrier 30 portions, respectively. Each unitary barrier 310, 320 provides a means of individual positioning and adhesive attachment to an existing diaper 200 via corresponding unitary adhesive strip 330 and wax paper 26 portions along a rear surface. Alternately, the unitary barriers 310, 320 can be affixed to an existing diaper 200 via other fastening means, such as Velcro®. The unitary barriers 310, 320 are intended to allow a user to accurately position each unitary barrier 310, 320 individually to a desired position, as well as provide a possible cost savings resulting from using only a single unitary barrier 310, 320 if so inclined. It is envisioned that the unitary barriers 310, 320 would be introduced being packaged and sold in combined and separate formats in various quantities based upon a user's preference and need. The unitary barriers 310, 320 can be integrated into the diaper 200 during manufacturing similar to the embodiment 100 illustrated in FIG. 4.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the device 10, it would be installed as indicated in FIGS. 1 and 3c. The method of installing and utilizing the device 10 may be achieved by performing the following steps: procuring a single unit or a package of the devices 10 being of an appropriate size with regards to a prospective wearer; attaching the device 10 to an existing diaper 200 by removing the wax paper portions 26 from the adhesive strips 24a, 24b, 24c; aligning the device 10 along an inner surface of said diaper 200 such that the rear barrier 20 is positioned slightly below a rear waistline portion 202 and the front barrier 30 is positioned slightly below the front waistline portion 204; affixing the device 10 to the diaper 200 by pressing upon an inner surface area being aligned with the adhesive strips 24a, 24b, 24c; installing the diaper 200 with the device 10 upon the wearer; fastening the diaper 200 around a waist area portion of the wearer using the tape fasteners 210; and, benefiting from improved containment of a bowel movement afforded a wearer of the device 10 even though the wearer may have occupied a seated position for a period of time.

The first alternate embodiment 100 of the present invention incorporates the insert 10 into the construction of the diaper assembly 200. The method of installing, utilizing, and benefiting from the first alternate embodiment 100 may be achieved in a similar manner as the preferred embodiment 10 by performing the steps described above which follow the installation of the device 10 within the diaper 200.

The method of installing and utilizing the second alternate embodiment 300 may be achieved by performing the following steps: procuring a quantity of unitary rear bathers 310 and/or a quantity of unitary front barriers 320; removing the wax paper layer 26 from the unitary adhesive strips 330; placing the unitary barriers 310, 320 upon an existing diaper assembly 200 at specific desired locations.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A containment insert configured to be removably placed on a diaper, comprising:
    an insert panel;
    a rear barrier affixed to said insert panel, said rear barrier comprising a body protruding outwardly from said insert panel and having generally inverted "V"-shape, in longitudinal cross-section, with an elevated center protrusion; and,
    a plurality of equidistantly-spaced lateral adhesive strips, each located on a rear surface of said insert panel capable of removable attachment to said diaper;
    wherein, when said insert panel is attached to said diaper, said rear barrier extends laterally across said diaper proximate to a rear waistband of said diaper;
    wherein, when said diaper is placed on a wearer, said rear barrier locates at a lumbar region of said wearer and said body conforms to a recessed contour of said lumbar region to absorb body fluids and physically prevent migration of said body fluids and waste materials beyond said insert panel.

2. The insert of claim 1, wherein said insert panel further comprises a front barrier, wherein when said diaper is placed on a wearer, said front barrier locates at an abdominal region of said wearer to absorb body fluids and physically prevent migration of said body fluids and waste materials beyond said insert panel.

3. The insert of claim 2, wherein said front barrier comprises an elevated form extending laterally across said diaper configured to correspond to said abdominal region.

4. The insert of claim 2, wherein said front barrier is affixed to said insert panel by means of at least one adhesive strip.

5. The insert of claim 2, wherein said front and said rear barriers are constructed of one of a group of soft and absorbent materials, said group includes polypropylene, cotton batting, and sodium polyacrylate.

6. The insert of claim 1, wherein said insert panel has an hour-glass perimeter shape.

7. The insert of claim 1, wherein said rear barrier is affixed to said insert panel by means of at least one adhesive strip.

8. A diaper assembly comprising a containment insert comprising;
    an insert panel having a rear barrier, said rear barrier comprising a body protruding outwardly from said insert panel and having generally inverted "V"-shape, in longitudinal cross-section, with an elevated center protrusion;
    a plurality of equidistantly-spaced lateral adhesive strips, each located on a rear surface of said insert panel capable of removable attachment to said diaper;
    a pair of front wings;
    a pair of rear wings; and,
    an attachment means adapted to operatively connect said rear wings and said front wings together to secure said diaper assembly about the body of a wearer;
    wherein, when said diaper assembly is placed on said wearer, said rear barrier locates at a lumbar region of said wearer and said body conforms to a recessed contour of said lumbar region to absorb body fluids and physically prevent migration of said body fluids and waste materials beyond said insert panel.

9. The assembly of claim 8, wherein said insert panel further comprises a front barrier, wherein when said diaper is placed on said wearer, said front barrier locates at an abdominal region of said wearer to absorb body fluids and physically prevent migration of said body fluids and waste materials beyond said insert panel.

10. The assembly of claim 8, wherein said insert panel has an hour-glass perimeter shape.

11. The assembly of claim 8, wherein said front barrier comprises an elevated form extending laterally across said diaper configured to correspond to said abdominal region.

* * * * *